(12) United States Patent
Yoshida

(10) Patent No.: US 12,065,176 B2
(45) Date of Patent: Aug. 20, 2024

(54) AUTONOMOUS VEHICLE EMERGENCY OPERATING MODE FOR COMMUNICATING WITH SURROUNDINGS AND SEEKING EMERGENCY MEDICAL ATTENTION

(71) Applicant: DENSO CORPORATION, Kariya (JP)

(72) Inventor: Ichiro Yoshida, Kariya (JP)

(73) Assignee: DENSO CORPORATION, Kariya (JP)

( * ) Notice: Subject to any disclaimer, the term of this patent is extended or adjusted under 35 U.S.C. 154(b) by 320 days.

(21) Appl. No.: 17/197,888

(22) Filed: Mar. 10, 2021

(65) Prior Publication Data

US 2021/0188322 A1 Jun. 24, 2021

Related U.S. Application Data

(63) Continuation of application No. PCT/JP2019/035219, filed on Sep. 6, 2019.

(30) Foreign Application Priority Data

Sep. 14, 2018 (JP) ................................ 2018-172500

(51) Int. Cl.
*A61B 5/00* (2006.01)
*B60Q 1/52* (2006.01)
(Continued)

(52) U.S. Cl.
CPC .... *B60W 60/0051* (2020.02); *B60W 60/0016* (2020.02); *G05D 1/0061* (2013.01); *G05D 1/0214* (2013.01); *B60W 2540/229* (2020.02)

(58) Field of Classification Search
CPC ......... B60W 60/0051; B60W 60/0016; B60W 2540/229; G05D 1/0061; G05D 1/0214
See application file for complete search history.

(56) References Cited

U.S. PATENT DOCUMENTS

2017/0090475 A1\* 3/2017 Choi ..................... A61B 5/18
2017/0105104 A1\* 4/2017 Ulmansky ............... H04W 4/42
(Continued)

FOREIGN PATENT DOCUMENTS

JP 2007249477 A 9/2007
JP 2009048605 A 3/2009
(Continued)

OTHER PUBLICATIONS

Machine Translation—KR20180108263A—Woo—Mar. 2017 (Year: 2017).\*

(Continued)

*Primary Examiner* — Jess Whittington
*Assistant Examiner* — Rami Nabih Bedewi
(74) *Attorney, Agent, or Firm* — Harness, Dickey & Pierce, P.L.C.

(57) ABSTRACT

A vehicle device monitors a physical condition of a driver, executes an awakening operation when detecting abnormal physical condition of the driver, determines whether the abnormal physical condition of the driver is resolved by the awakening operation, executes an emergency autonomous travelling when the abnormal physical condition of the driver being determined to be not resolved, notifies the emergency autonomous travelling toward vehicle surrounding, executes a rescue request in travelling state toward the vehicle surrounding during the emergency autonomous travelling, searches for a facility capable of treating the abnormal physical condition of the driver and sets the facility as a destination, sets another facility as a destination when no facility capable of treating the abnormal physical condition of the driver being specified, and executes a rescue request after arrival toward the vehicle surrounding in response to the vehicle arriving at another facility.

8 Claims, 12 Drawing Sheets

(51) Int. Cl.
  *B60W 60/00* (2020.01)
  *G01C 21/34* (2006.01)
  *G05D 1/00* (2006.01)
  *G08G 1/09* (2006.01)
  *G08G 1/16* (2006.01)

(56) References Cited

U.S. PATENT DOCUMENTS

| | | | |
|---|---|---|---|
| 2017/0106876 A1* | 4/2017 | Gordon | B60W 50/082 |
| 2017/0322558 A1* | 11/2017 | Teshima | B60Q 5/00 |
| 2018/0043901 A1* | 2/2018 | Kim | A61B 5/747 |
| 2018/0120837 A1* | 5/2018 | Regmi | A61B 5/11 |
| 2018/0315298 A1* | 11/2018 | Kitamura | G08B 25/014 |
| 2020/0275249 A1* | 8/2020 | Kim | H04W 4/12 |

FOREIGN PATENT DOCUMENTS

| | | | | |
|---|---|---|---|---|
| JP | 2016009248 A | | 1/2016 | |
| JP | 2016091309 A | | 5/2016 | |
| JP | 2017188127 A | | 10/2017 | |
| JP | 2018043705 A | | 3/2018 | |
| KR | 20180108263 A | * | 3/2017 | B60K 28/06 |
| KR | 20180108263 A | * | 3/2017 | B60K 28/06 |

OTHER PUBLICATIONS

KR 20180108263 A—Machine Translation—Woo—Mar. 24, 2017 (Year: 2017).*
Machine Translation—KR20180108263A (Year: 2017).*

* cited by examiner

AUTONOMOUS VEHICLE EMERGENCY OPERATING MODE FOR COMMUNICATING WITH SURROUNDINGS AND SEEKING EMERGENCY MEDICAL ATTENTION

CROSS REFERENCE TO RELATED APPLICATIONS

The present application is a continuation application of International Patent Application No. PCT/JP2019/035219 filed on Sep. 6, 2019, which designated the U.S. and claims the benefit of priority from Japanese Patent Application No. 2018-172500 filed on Sep. 14, 2018. The entire disclosures of all of the above applications are incorporated herein by reference.

TECHNICAL FIELD

The present disclosure relates to a vehicle device and a drive assist program product.

BACKGROUND

There has been known a vehicle device which monitors a physical condition of a driver during driving, and when the driver's physical condition is specified to be abnormal, a warning is sent to the surrounding of the vehicle.

SUMMARY

The present disclosure provides a vehicle device that monitors a physical condition of a driver in a driving state of a vehicle, executes an awakening operation in response to the physical condition of the driver being determined to be abnormal, determines whether the abnormal physical condition of the driver is resolved by execution of the awakening operation, executes an emergency autonomous travelling of the vehicle by controlling the vehicle to travel in an autonomous travelling mode in response to the abnormal physical condition of the driver being determined to be not resolved, notifies a surrounding of the vehicle that the vehicle is in a state of the emergency autonomous travelling while the emergency autonomous travelling being executed, executes a rescue request in travelling state toward the surrounding of the vehicle while the emergency autonomous travelling being executed, searches for a facility capable of treating the abnormal physical condition of the driver in response to the abnormal physical condition of the driver being determined to be not resolved, sets the facility capable of treating the abnormal physical condition of the driver as a destination in response to the facility capable of treating the abnormal physical condition of the driver being specified, sets another facility as a destination in response to no facility capable of treating the abnormal physical condition of the driver being specified, and executes a rescue request after arrival toward the surrounding of the vehicle in response to the vehicle arriving at another facility and being stopped.

BRIEF DESCRIPTION OF DRAWINGS

Objects, features and advantages of the present disclosure will become apparent from the following detailed description made with reference to the accompanying drawings. In the drawings.

DETAILED DESCRIPTION

Figure 1:
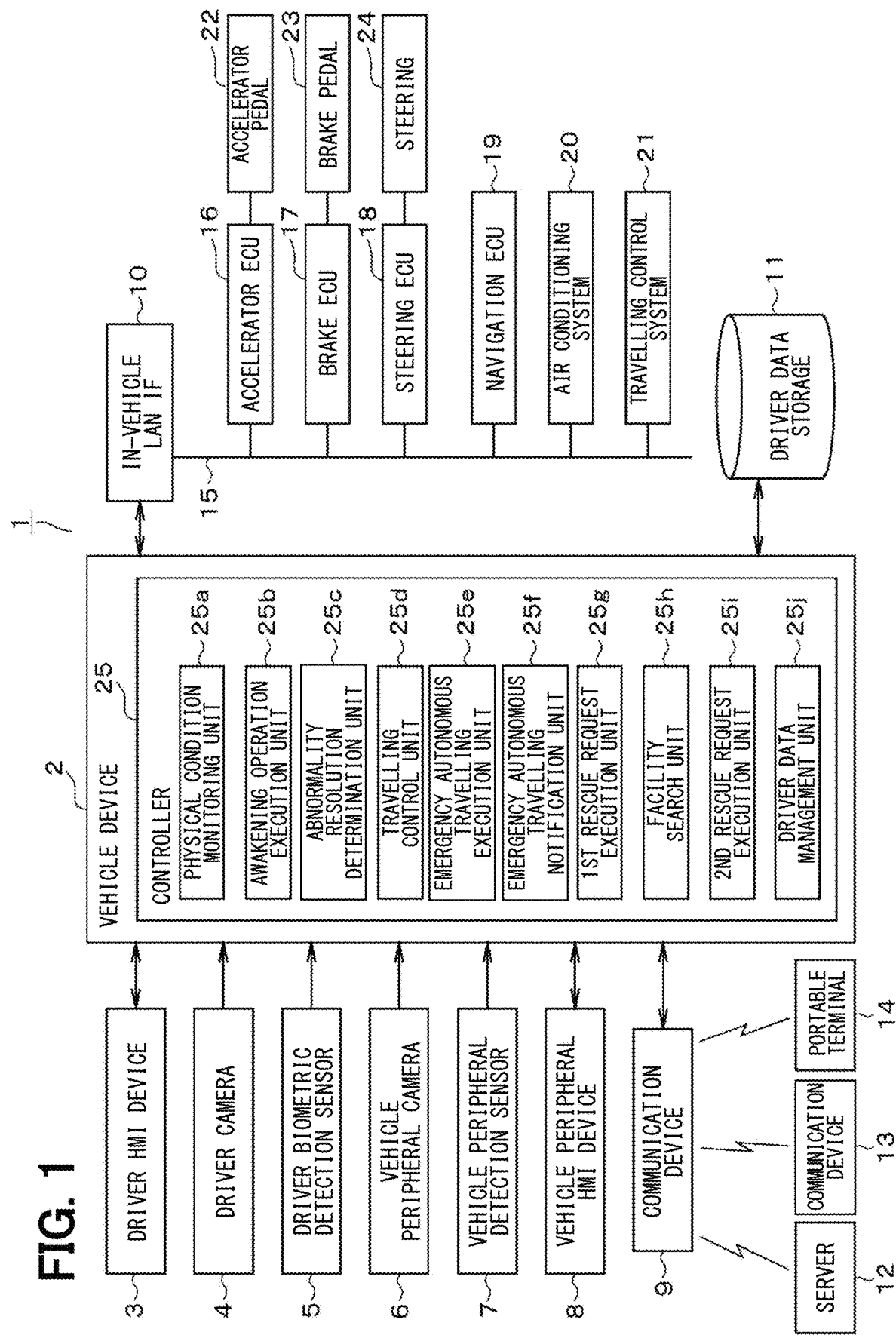
FIG. 1 is a block diagram showing an embodiment of the present disclosure.
Figure 2:
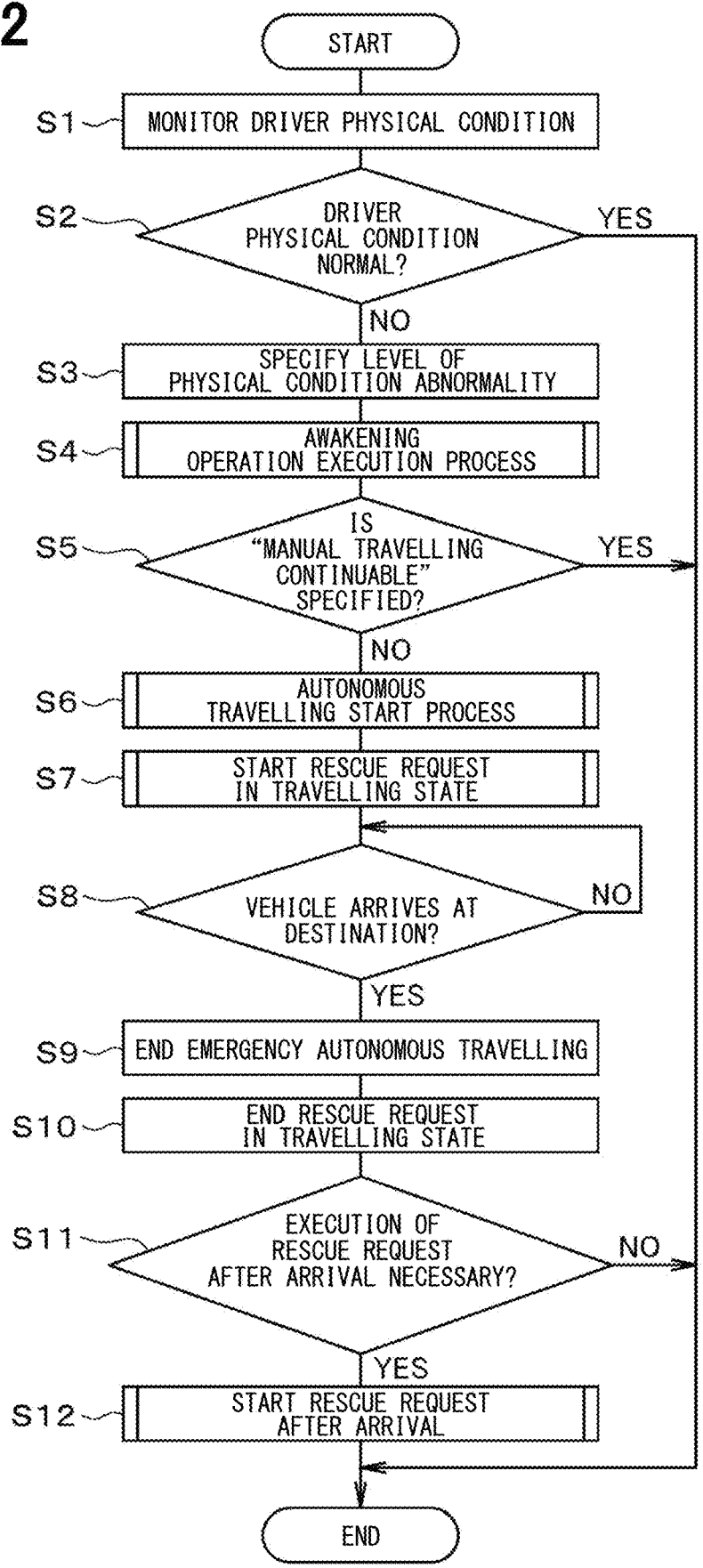
FIG. 2 is a flowchart showing a driver monitoring process.
Figure 3:
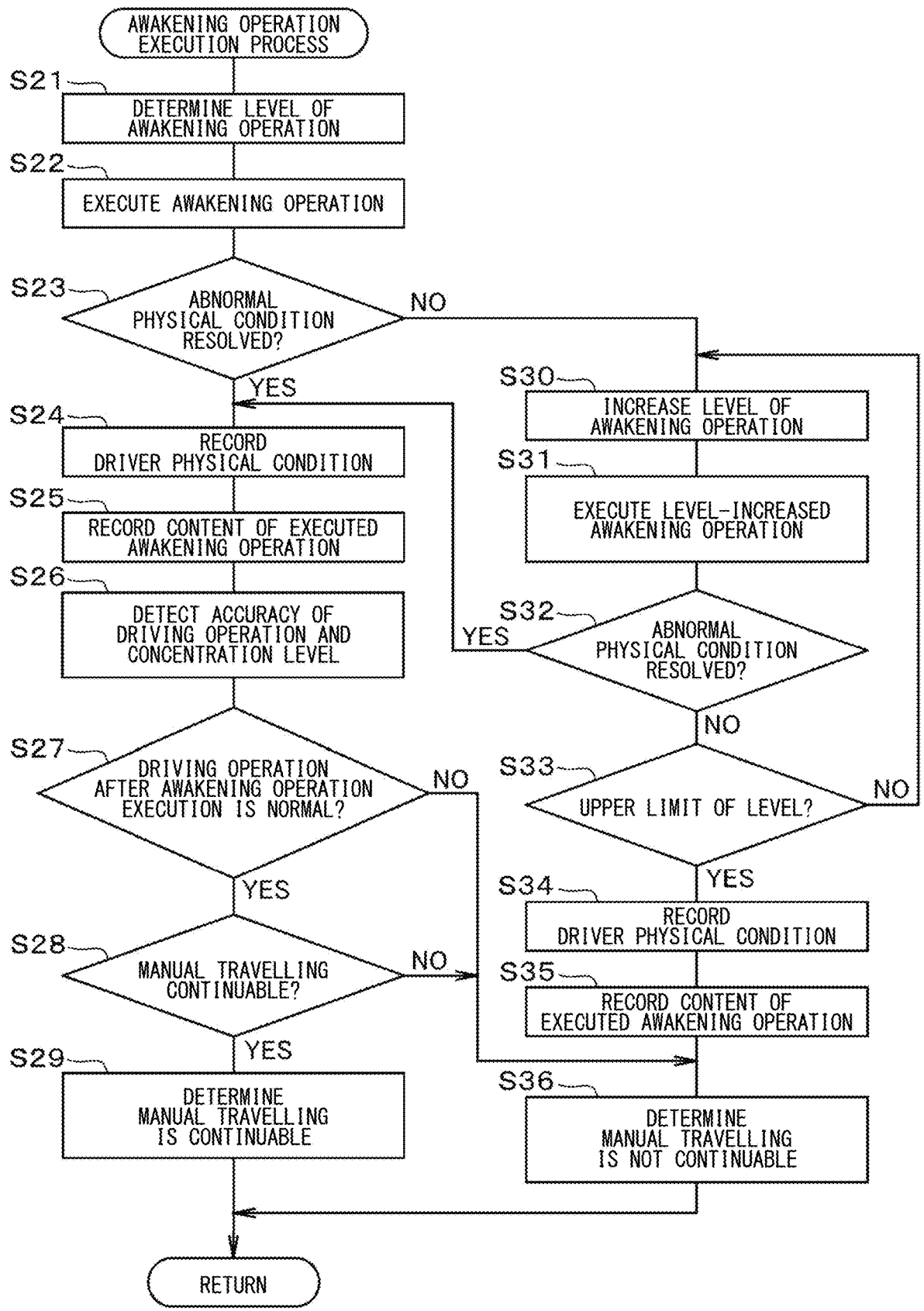
FIG. 3 is a flowchart showing an awakening operation execution process.
Figure 4:
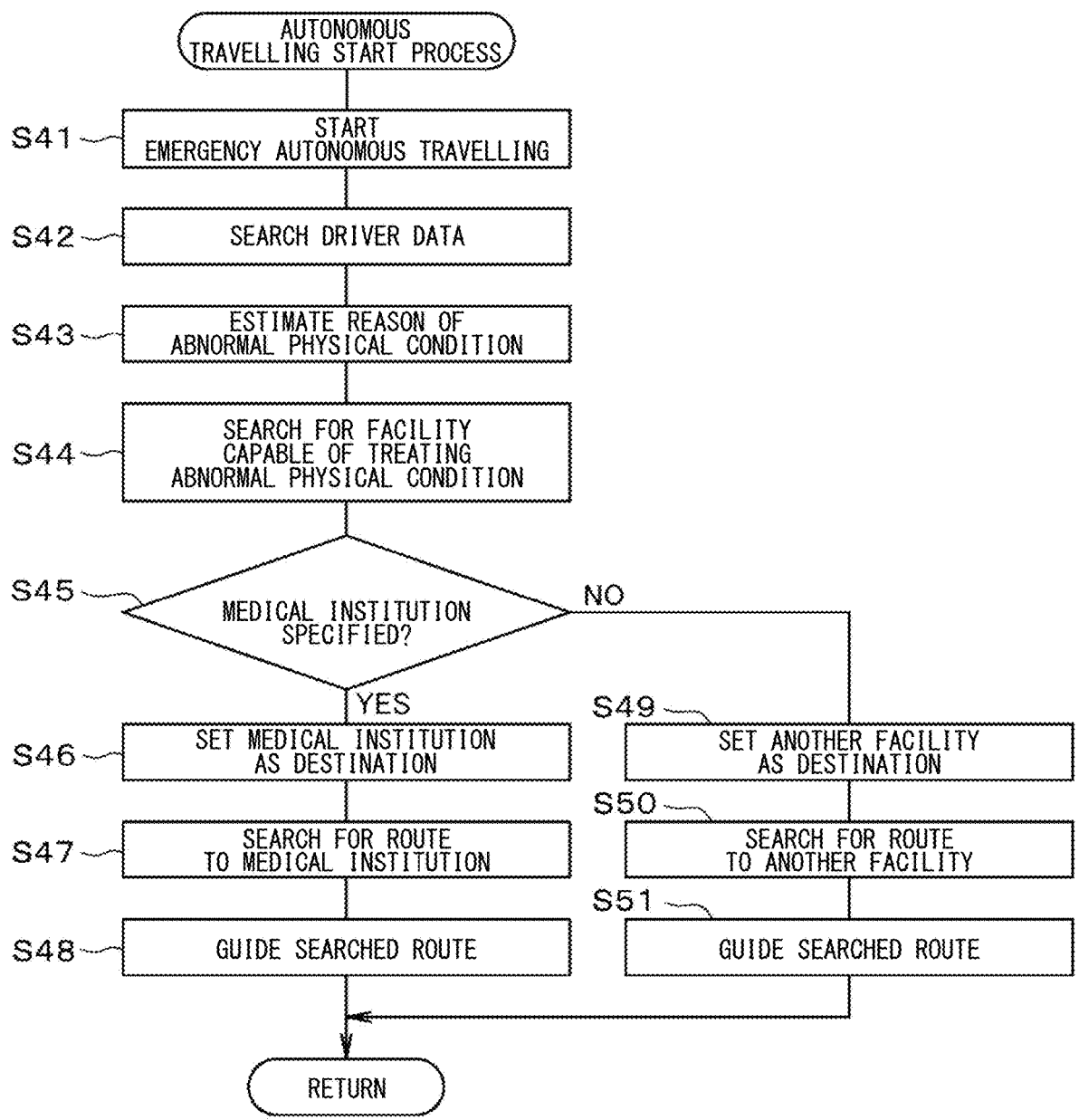
FIG. 4 is a flowchart showing an autonomous travelling start process.
Figure 5:
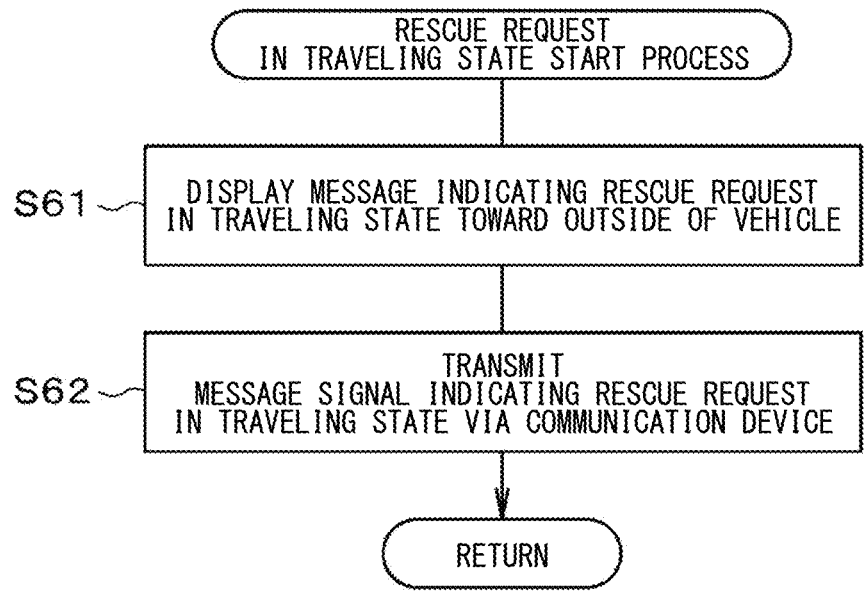
FIG. 5 is a flowchart showing a rescue request start process in a traveling state.
Figure 6:
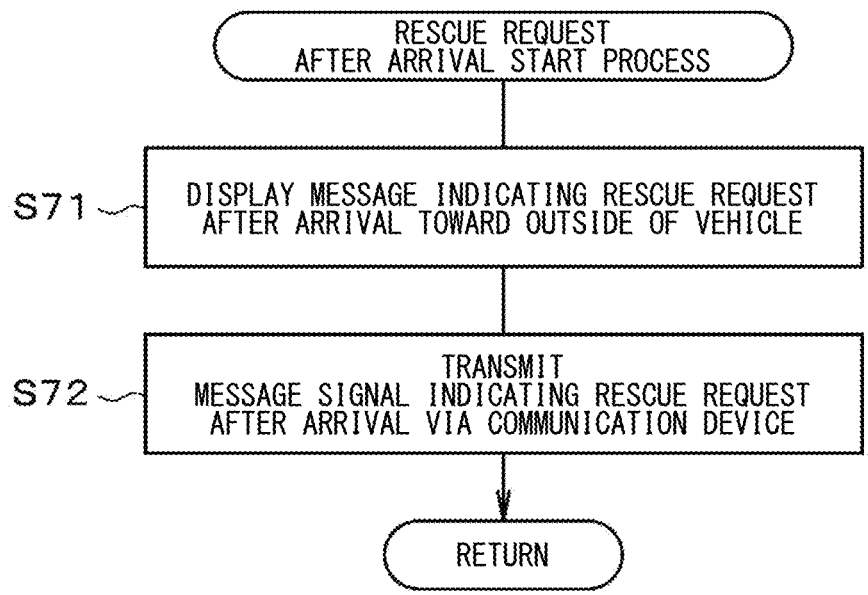
FIG. 6 is a flowchart showing a rescue request start process after arrival.

Various technologies have been proposed to assist a driving of a vehicle. It has been known that a physical condition of a driver is monitored during the driving, and when the driver's physical condition is specified to be abnormal, a warning is sent to the surrounding of the vehicle. In response to no obstacle being detected around the vehicle, the vehicle applies brake control to stop the vehicle.

In the above configuration, in response to no obstacle being detected around the vehicle, the vehicle is controlled to be stopped by applying a brake control in order to avoid, in advance, a confusion or an accident around the vehicle. However, it is difficult to how to control the vehicle in a case of detecting an obstacle around the vehicle. Suppose that the vehicle does not apply the brake control in a case of detecting an obstacle around the vehicle. Then, the vehicle will continue to run with the driver who is in an abnormal physical condition and may cause confusion or an accident around the vehicle. With consideration of this point, a mechanism is required to take an appropriate measure in response to a detection of a driver's abnormal physical condition in a travelling state of the vehicle with consideration of the surroundings of the vehicle.

According to an aspect of the present disclosure, a vehicle device includes: a physical condition monitoring unit configured to monitor a physical condition of a driver in a driving state of a vehicle; an awakening operation execution unit configured to execute an awakening operation in response to the physical condition of the driver being determined to be abnormal by the physical condition monitoring unit; an abnormality resolution determination unit configured to determine whether the abnormal physical condition of the driver is resolved by the awakening operation executed by the awakening operation execution unit; a travelling control unit configured to control the vehicle to travel in a manual travelling mode or in an autonomous travelling mode; an emergency autonomous travelling execution unit configured to execute an emergency autonomous travelling of the vehicle by instructing the travelling control unit to control the vehicle travel in the autonomous travelling mode in response to the abnormality resolution determination unit determining that the abnormal physical condition of the driver is not resolved; an emergency autonomous travelling notification unit configured to notify a surrounding of the vehicle that the vehicle is in a state of the emergency autonomous travelling while the emergency autonomous travelling execution unit executes the emergency autonomous travelling of the vehicle; a first rescue request execution unit configured to execute a rescue request in travelling state toward the surrounding of the vehicle while the emergency autonomous travelling execution unit executes the emergency autonomous travelling of the vehicle; a facility search unit configured to search for a facility capable of treating the abnormal physical condition of the driver in response to the abnormality resolution determination unit determining that the abnormal physical condition of the driver is not resolved; and a second rescue request execution unit configured to execute a rescue request after arrival toward the surrounding of the vehicle in response to the vehicle arriving at another facility and being stopped, the rescue request after arrival being different from the rescue request in travelling state. The emergency autonomous travelling execution unit sets the facility specified by the facility search unit as a destination in response to the facility search unit specifying the facility capable of treating the abnormal physical condition of the driver, and executes the emergency autonomous travelling of the vehicle to the destination. The emergency autonomous travelling execution unit sets another facility as a destination in response to the facility search unit failing to specify the facility capable of treating the abnormal physical condition of the driver, and executes the emergency autonomous travelling of the vehicle to the destination.

According to another aspect of the present disclosure, a drive assist program product, which is stored in a tangible non-transitory computer-readable storage medium and comprising instructions to be executed by a controller of a vehicle device, is provided. The instructions included in the drive assist program product includes: monitoring a physical condition of a driver in a driving state of a vehicle; executing an awakening operation in response to the physical condition of the driver being determined to be abnormal; determining whether the abnormal physical condition of the driver being resolved by an execution of the awakening operation; executing an emergency autonomous travelling of the vehicle by controlling the vehicle to travel in an autonomous travelling mode in response to the abnormal physical condition of the driver being determined to be not resolved by the execution of the awakening operation; notifying a surrounding of the vehicle that the vehicle is in a state of the emergency autonomous travelling while the emergency autonomous travelling being executed; executing a rescue request in travelling state toward the surrounding of the vehicle while the emergency autonomous travelling being executed; searching for a facility capable of treating the abnormal physical condition of the driver in response to the abnormal physical condition of the driver being determined to be not resolved; setting the facility capable of treating the abnormal physical condition of the driver as a destination in response to the facility capable of treating the abnormal physical condition of the driver being specified and executing the emergency autonomous travelling of the vehicle to the destination; setting another facility as a destination in response to no facility capable of treating the abnormal physical condition of the driver being specified and executing the emergency autonomous travelling of the vehicle to the destination; and executing a rescue request after arrival toward the surrounding of the vehicle in response to the vehicle arriving at another facility and being stopped, the rescue request after arrival being different from the rescue request in travelling state.

When the driver's physical condition becomes abnormal in the travelling state, an awakening operation is executed. When the driver's abnormal physical condition is not resolved even after the awakening operation is executed, instead of applying a brake control to stop the vehicle, the vehicle is controlled to travel in the autonomous travelling mode for executing the emergency autonomous travelling. By activating an autonomous driving of the vehicle while ensuring the safety around the vehicle, it is possible to avoid a situation which may cause confusion or an accident around the vehicle. As a result, when the driver's physical condition is specified to be abnormal in a travelling state of the vehicle, appropriate measures can be taken with consideration of the influence of the vehicle to the surrounding of the vehicle.

The following will describe an embodiment of the present disclosure with reference to the accompanying drawings. A vehicle system 1 mounted on a vehicle is a drive assist system, and the drive assist system monitors a physical condition of a driver and implements appropriate measures according to the monitoring result. As shown in FIG. 1, the vehicle system 1 includes a vehicle device 2, a driver HMI (Human Machine Interface) device 3, a driver camera 4, a driver biometric detection sensor 5, a vehicle peripheral camera 6, a vehicle peripheral detection sensor 7, a vehicle peripheral HMI device 8, a communication device 9, an in-vehicle LAN (Local Area Network) interface 10, and a driver data storage 11. The vehicle system 1 may be mounted on a vehicle at a manufacturing stage, or mounted on the vehicle after the vehicle is shipped to a market.

The driver HMI device 3 includes, for example, a microphone, a camera, a speaker, a display, or the like. In response to the driver HMI device 3 receiving a dialogue command signal from the vehicle device 2, the driver HMI device 3 performs a dialogue with the driver by activating a dialogue agent function with reference to the dialogue command signal. That is, the driver HMI device 3 collects a voice made by the driver with a microphone, recognizes the voice, analyzes a facial expression of the driver taken by a camera, outputs an audio signal to the driver through a speaker, and displays an image to the driver on a display device. The driver HMI device 3 performs a dialogue with the driver by the dialogue agent function, and outputs a result of the dialogue to the vehicle device 2. The dialogue between the driver HMI device 3 and the driver may be performed with use of artificial intelligence (AI) technology. The camera used in the driver HMI device 3 may be provided by the driver camera 4.

The driver camera 4 is placed inside the vehicle and capture a range including a face of the driver seated in a driver seat. The driver camera 4 outputs, to the vehicle device 2, an image signal including the captured images. The driver camera 4 may include, for example, a CCD (charge coupled device) image sensor, a CMOS (complementary metal oxide semiconductor) image sensor, or the like. The number of the driver camera 4 may be one or multiple.

The driver biometric detection sensor 5 is configured to detect biometric information such as the driver's pulse, heart rate, blood pressure, and brain activity status. The driver biometric detection sensor 5 outputs a sensor signal including the detected sensor value to the vehicle device 2.

The vehicle peripheral camera 6 is positioned so that a vehicle peripheral area can be captured by the camera, and outputs an image signal including the captured image to the vehicle device 2. The vehicle peripheral camera 6 may be provided by a CCD image sensor, a CMOS image sensor, or the like. The number of the vehicle peripheral camera 6 may be one or multiple.

The vehicle peripheral detection sensor 7 is configured to detect the vehicle peripheral, and may include a millimeter-wave radar, a LIDAR (Light Detection and Ranging), and a sonar. The vehicle peripheral detection sensor 7 outputs a sensor signal including the detected sensor value to the vehicle device 2.

The vehicle peripheral HMI device 8 includes, for example, a microphone, a camera, a speaker, a display, or the like. In response to the vehicle peripheral HMI device 8 receiving a dialogue command signal from the vehicle device 2, the vehicle peripheral HMI device 8 performs a dialogue with a person who is close to the vehicle by activating a dialogue agent function with reference to the dialogue command signal. That is, the vehicle peripheral HMI device 8 collects a voice made by the person who is close to the vehicle with a microphone, recognizes the voice, analyzes a facial expression of the person who is close to the vehicle taken by a camera, outputs an audio signal to the person who is close to the vehicle through a speaker, and displays an image to the person who is close to the vehicle on a display device. The vehicle peripheral HMI device 8 performs a dialogue with the person who is close to the vehicle by the dialogue agent function, and outputs a result of the dialogue to the vehicle device 2. Dialogue with person who is close to the vehicle may be carried out by using artificial intelligence technology.

The communication device 9 includes, for example, a communication unit installed on the vehicle, a portable terminal having a communication function and carried by the driver into the vehicle compartment, or the like. The communication device 9 performs a wireless communication, based on a predetermined wireless communication standard, with a server 12 outside the vehicle, a communication device 13 mounted on a different vehicle, a portable terminal 14 carried by a pedestrian, or the like. The predetermined wireless communication standard includes, for example, WiFi (wireless fidelity, registered trademark), LTE (long term evolution, registered trademark), V2X (vehicle to everything), DSRC (dedicated short range communication, registered trademark), LPWA (low power wide area), or the like. In response to receiving a transmission instruction signal from the vehicle device 2, the communication device 9 transmits a transmission signal to the server 12, the communication device 13 of different vehicle, and the portable terminal 14 carried by the pedestrian in accordance with the transmission instruction signal. In response to receiving, as a reception signal, a transmission signal transmitted from the server 12, the communication device 13 of different vehicle, or the portable terminal 14 of the pedestrian, the communication device 9 outputs a reception detection signal to the vehicle device 2.

The in-vehicle LAN interface 10 is connected, via an in-vehicle LAN 15, with an accelerator ECU (electronic control unit) 16, a brake ECU 17, a steering ECU 18, a navigation ECU 19, an air conditioning system 20, and a travelling control system 21.

The accelerator ECU 16 detects an operation amount of an accelerator pedal 22, and outputs a detection signal indicating the detected operation amount to the vehicle device 2. The brake ECU 17 detects an operation amount of a brake pedal 23, and outputs a detection signal indicating the detected operation amount to the vehicle device 2. The steering ECU 18 detects an operation amount of a steering wheel 24, and outputs a detection signal indicating the detected operation amount to the vehicle device 2.

In response to the navigation ECU 19 receiving a search signal from the vehicle device 2, the navigation ECU 19 searches for a facility designated as a search target by the search signal based on a current position of the vehicle. When a search target facility exists around the vehicle and the search target facility is specified, the navigation ECU 19 sets the specified search target facility as a destination, searches for a route from the current position of the vehicle to the destination, and performs a route guidance according to the searched route from the current position of the vehicle to the destination. When a search target facility does not exist around the vehicle or the search target facility is not specified, the navigation ECU 19 sets another facility different from the search target facility as a destination, searches for a route from the current position of the vehicle to the destination, and performs a route guidance according to the searched route from the current position of the vehicle to the destination.

In a case where the search target facility is a medical institution, the navigation ECU 19 sets the medical institution as a destination under a condition that the medical institution exists around the vehicle, searches for a route from the current position of the vehicle to the medical institution, and performs the route guidance according to the searched route. In a case where the medical institution does not exist around the vehicle, the navigation ECU 19 sets a facility different from the medical institution as a destination, searches for a route from the current position of the vehicle to the facility, and performs a route guidance according to the searched route. The facility different from a medical institution may include a facility where an ambulance can easily arrive, a facility having a vast site where an emergency helicopter can easily land. Such facility may include a public facility such as a school or a park.

In response to the air conditioning system 20 receiving a control signal from the vehicle device 2, the air conditioning system 20 controls air conditioning in accordance with the received control signal. The air conditioning system 20 controls, for example, temperature, air blow amount, air blow direction as the control of air conditioning. The air conditioning system 20 stimulates the driver by controlling the air conditioning. Such controlling of air conditioning may include increase of air amount directed to the driver, change of air blow directing toward the driver, or the like.

In response to the travelling control system 21 receiving a control signal from the vehicle device 2, the travelling control system 21 performs a travelling control in accordance with the received control signal. In response to receiving a manual travelling mode signal from the vehicle device 2, the travelling control system 21 performs the travelling control in a manual travelling mode. In response to receiving an autonomous travelling mode signal from the vehicle device 2, the travelling control system 21 performs the travelling control in an autonomous travelling mode. The manual travelling mode indicates a mode in which the vehicle travels according to a driver's manipulation on the accelerator, the brake, or the steering wheel. The autonomous travelling mode indicates a mode in which the vehicle travels autonomously without a driver's manipulation on the accelerator, the brake, or the steering wheel.

When the travelling control system 21 performs the travelling control in the autonomous travelling mode, a situation around the vehicle is specified using the image included in the image signal, which is output from the vehicle peripheral camera 6 to the vehicle device 2, and analysis result of a sensor signal, which is output from the vehicle peripheral detection sensor 7 to the vehicle device 2. In response to the travelling control system 21 specifying the situation around the vehicle, the travelling control system determines a traveling track to avoid obstacles (other vehicles, pedestrians, etc.) existing on the road, and performs the traveling control according to the determined traveling track. Thus, the travelling control system 21 can suppress occurrence of confusion or accident around the vehicle by avoiding obstacles on the road and ensuring safety around the vehicle during the autonomous travelling mode.

The driver data storage 11 is configured to store various data related to the driver. Specifically, the driver data storage 11 may store, as various data related to the driver, medical history, hospital visit history, or the like in addition to gender, age, or the like.

In the present embodiment, as illustrated in FIG. 1, the driver HMI device 3, the vehicle peripheral HMI device 8, and the communication device 9 are provided separately from the vehicle device 2. Alternatively, the function of the driver HMI device 3, the function of the vehicle peripheral HMI device 8, and the function of the communication device 9 may be incorporated in the vehicle device 2. The present embodiment exemplifies a configuration in which the air conditioning system 20 and the travelling control system 21 are connected to the vehicle device 2 via the in-vehicle LAN 15. Alternatively, the air conditioning system 20 and the travelling control system 21 may be directly connected to the vehicle device 2 without the in-vehicle LAN 15.

The vehicle device 2 includes a controller 25 that is provided by a microcomputer having a CPU (Central Process Unit), a ROM (Read Only Memory), a RAM (Random Access Memory), and an I/O (Input/Output). The controller 25 executes a computer program stored in a non-transitory tangible storage medium to execute a process corresponding to the computer program, and controls the overall operation of the vehicle device 2. The computer program executed by the controller 25 includes a drive assist program.

The controller 25 includes a physical condition monitoring unit 25a, an awakening operation execution unit 25b, an abnormality resolution determination unit 25c, a travelling control unit 25d, an emergency autonomous travelling execution unit 25e, an emergency autonomous travelling notification unit 25f, a first rescue request execution unit 25g, a facility search unit 25h, a second rescue request execution unit 25i, and a driver data management unit 25j. Blocks of these functions correspond to the processing of computer program executed by the microcomputer.

The physical condition monitoring unit 25a monitors the physical condition of the driver during the travelling of the vehicle. The physical condition monitoring unit 25a monitors the driver's physical condition using the dialogue agent function provided by the driver HMI device 3, an image signal output from the driver camera 4 to the vehicle device 2, and a sensor signal output from the driver biometric detection sensor 5 to the vehicle device 2.

In a case where the dialogue agent function of the driver HMI device 3 is used, the physical condition monitoring unit 25a monitors the physical condition of the driver as follows. The physical condition monitoring unit 25a learns the situation of the dialogue provided by the dialogue agent function in a normal state of the driver, quantifies the learning result, and stores the quantified learning result. The physical condition monitoring unit 25a compares a numerical value indicating the dialogue by the current dialogue agent function in the current state of the driver with a numerical value indicating the dialogue by the dialogue agent function in the normal state of the driver, and determines that the dialogue is performed normally in response to the difference being less than a threshold value set in advance. In response to the difference being equal to or greater than the threshold value, the physical condition monitoring unit 25a determines that the dialogue is not performed normally and the driver's physical condition is specified to be abnormal.

In a case where the image signal output from the driver camera 4 to the vehicle device 2 is used, the physical condition monitoring unit 25a monitors the physical condition of the driver as follows. The physical condition monitoring unit 25a analyzes the image included in the image signal output from the driver camera 4 to the vehicle device 2, and determines an eye opening degree of the driver based on, for example, a shape of an upper eyelid or a distance between the upper eyelid and a lower eyelid. The physical condition monitoring unit 25a may also determine a movement frequency of driver's sight line based on movement of driver's eyeball. The physical condition monitoring unit 25a learns the distance between the upper eyelid and the lower eyelid of the driver in the normal state of the driver, quantifies the learning result, and stores the quantified learning result. The physical condition monitoring unit 25a compares a value indicating the current eye opening degree of the driver with the value of the driver's eye opening degree in the normal state, and in response to the difference being less than a threshold value set in advance, specifies that the driver is in the normal physical condition. In response to the difference being equal to or greater than the threshold value, the physical condition monitoring unit 25a determining that the driver's physical condition is abnormal. The physical condition monitoring unit 25a learns the movement frequency of driver's sight line in the normal state of the driver, quantifies the learning result, and stores the quantified learning result. The physical condition monitoring unit 25a compares a value indicating the current movement frequency of driver's sight line with the value of the movement frequency of driver's sight line in the normal state, and in response to the difference being less than a threshold value set in advance, specifies that the driver is in the normal physical condition. In response to the difference being equal to or greater than the threshold value, the physical condition monitoring unit 25a determining that the driver's physical condition is abnormal. The physical condition monitoring unit 25a also assumes a case where the driver's posture may be significantly deformed depending on the level of the driver's physical condition abnormality. Thus, in a case where the driver's face cannot be recognized from the image included in the image signal, the physical condition of the driver may be specified as the abnormal.

In a case where the sensor signal output from the driver biometric detection sensor 5 to the vehicle device 2 is used, the physical condition monitoring unit 25a monitors the physical condition of the driver as follows. The physical condition monitoring unit 25a determines, by analyzing the sensor signal output from the driver biometric detection sensor 5 to the vehicle device 2, the driver's pulse, heart rate, blood pressure, state of brain activity, or the like, and monitors the physical condition of the driver during travelling of the vehicle. The physical condition monitoring unit 25a learns a value of the sensor signal in the normal state of the driver, and stores the learned value. The physical condition monitoring unit 25a compares a value indicating the sensor signal in the current state with the value of sensor signal in the normal state, and in response to the difference being less than a threshold value set in advance, specifies that the driver is in the normal physical condition. In response to the difference being equal to or greater than the threshold value, the physical condition monitoring unit 25*a* determining that the driver's physical condition is abnormal.

The physical condition monitoring unit 25*a* may monitor the driver's physical condition using the dialogue agent function provided by the driver HMI device 3, the image signal output from the driver camera 4 to the vehicle device 2, and the sensor signal output from the driver biometric detection sensor 5 to the vehicle device 2 in combined manner as necessary. Alternatively, the physical condition monitoring unit 25*a* may monitor the driver's physical condition (i) only using the dialogue agent function provided by the driver HMI device 3, (ii) only using the image signal output from the driver camera 4 to the vehicle device 2, or (iii) only using the sensor signal output from the driver biometric detection sensor 5 to the vehicle device 2. In a case where the driver's physical condition is monitored using multiple devices in combined manner, an accuracy of specifying the driver's physical condition abnormality can be substantially improved. Alternatively, the physical condition monitoring unit 25*a* may monitor the physical condition of the driver by analyzing a reaction speed of the driver's accelerator operation, brake operation, steering operation or the like.

The awakening operation execution unit 25*b* executes an awakening operation in response to the driver's physical condition being specified to be abnormal by the physical condition monitoring unit 25*a*. The awakening operation execution unit 25*b* performs the awakening operation by outputting a notification command signal to the driver HMI device 3, and outputs an awakening sound from the speaker to stimulate the driver. For another example, the awakening operation execution unit 25*b* may output a control signal to the air conditioning system 20 to control the air conditioning so that an air volume directed toward the driver is increased or the direction of air blow is directed toward the driver, and awakens the driver by applying the stimulus. For another example, as the awakening operation, the awakening operation execution unit 25*b* may control the seat to vibrate in addition to output of the awakening sound from the speaker, increase of the air volume toward the driver, or direction change of the air blow toward the driver.

The abnormality resolution determination unit 25*c* determines whether the driver's physical condition abnormality has been resolved by the awakening operation executed by the awakening operation execution unit 25*b*. The abnormality resolution determination unit 25*c* determines that the driver's physical condition abnormality has not been resolved in response to, for example, the difference between the currently measured value and the value in the normal state continuing to equal to or greater than the threshold value. In response to the difference decreasing from a value equal to or greater than the threshold value to a value less than the threshold value and the state in which the difference maintains the value less than the threshold value continues for a certain period of time, the abnormality resolution determination unit 25*c* may determine that the driver's physical condition abnormality is resolved.

The travelling control unit 25*d* outputs the manual travelling mode signal to the travelling control system 21 to control the vehicle travel in the manual travelling mode. The travelling control unit 25*d* outputs an autonomous travelling mode signal to the travelling control system 21 to control the vehicle travel in the autonomous travelling mode.

In response to the abnormality resolution determination unit 25*c* determining that the driver's physical condition maintains abnormal state without being resolved, the emergency autonomous travelling execution unit 25*e* executes the emergency autonomous travelling by controlling the travelling control unit 25*d* to output the autonomous travelling mode signal to the travelling control system 21.

The emergency autonomous travelling notification unit 25*f* outputs a notification command signal to the vehicle peripheral HMI device 8 in a state where the emergency autonomous travelling execution unit 25*e* is performing the emergency autonomous travelling, and notifies the surrounding of the vehicle that emergency autonomous travelling is being executed.

The first rescue request execution unit 25*g* outputs a notification command signal to the vehicle peripheral HMI device 8 in a state where the emergency autonomous travelling execution unit 25*e* is performing the emergency autonomous travelling, and requests for the rescue toward the surrounding of vehicle during the emergency autonomous travelling. In this case, the first rescue request execution unit 25*g* executes the rescue request toward the surrounding of vehicle by the dialogue agent function in the travelling state. By executing the rescue request toward the surrounding of vehicle by the dialogue agent function in the travelling state, a person who is close to the vehicle can be notified of that the vehicle in the travelling state is requesting for a rescue, and can be notified of an occurrence of emergency.

The facility search unit 25*h* searches for a facility that can treat the driver's physical condition abnormality in response to the abnormality resolution determination unit 25*c* determines that the driver's physical condition abnormality has not been resolved. The facility search unit 25*h* outputs a search signal to the navigation ECU 19, and controls the navigation ECU 19 to search for a facility that can treat the driver's physical condition abnormality. In this case, when a medical institution is specified as the facility that can treat the driver's physical condition abnormality, the emergency autonomous travelling execution unit 25*e* sets the specified medical institution as the destination, and executes the emergency autonomous travelling of the vehicle to the medical institution set as the destination. When failing to find a medical institution as the facility that can treat the driver's physical condition abnormality and a school is specified as the facility different from the medical institution, the emergency autonomous travelling execution unit 25*e* sets the specified school as the destination, and executes the emergency autonomous travelling of the vehicle to the school set as the destination.

The second rescue request execution unit 25*i* outputs a notification command signal to the vehicle peripheral HMI device 8 after the vehicle arrives at the facility different from the medical institution, and requests for the rescue toward the surrounding of vehicle after arrival. In this case, the second rescue request execution unit 25*i* executes the rescue request toward the surrounding of vehicle by the dialogue agent function after arrival. By executing the rescue request toward the surrounding of vehicle by the dialogue agent function after arrival, a person around the vehicle can be notified of that the vehicle after arrival is requesting for a rescue, and can be notified of an occurrence of emergency.

The driver data management unit 25*j* manages the driver data stored in the driver data storage 11, stores new driver data in the driver data storage 11, or updates already stored driver data in the driver data storage 11.

The following will describe an operation of the above configuration with reference to FIG. 2 to FIG. 13. The following will describe an example in which the dialogue agent function of the driver HMI device 3 is used to monitor the physical condition of the driver.

In the vehicle device 2, the controller 25 executes a driver monitoring process at a predetermined cycle (for example, every several milliseconds) in an on state of an ignition switch. When a start event of the driver monitoring process is established, the controller 25 starts the driver monitoring process, monitors the physical condition of the driver by the dialogue agent function of the driver HMI device 3 (S1, physical condition monitoring procedure), and determines whether the physical condition of the driver is normal (S2). In response to the controller 25 determining that the dialogue is performed normally and determining that the physical condition of the driver is normal (S2: YES), the controller 25 ends the current driver monitoring process, and waits for establishment of the start event of the next driver monitoring process.

In response to the controller determining that the dialogue is performed abnormally and determining that physical condition of the driver is abnormal (S2: NO), the controller 25 switches from a normal dialogue mode to an abnormal dialogue mode and specifies a level of the physical condition abnormality of the driver (S3). For example, the controller 25 may ask the driver a question prepared in advance, comprehensively determines the content of the driver's answer to the question and the time required to answer the question, and specifies the level of physical condition abnormality. The controller 25 determines that the level of physical condition abnormality is relatively low in response to the content of the answer being appropriate or the time required to answer the question being relatively short. The controller 25 determines that the level of physical condition abnormality is relatively high in response to the content of the answer being inappropriate or the time required to answer the question being relatively long. In response to the controller 25 specifying the physical condition abnormality of the driver, the image signal output from the driver camera 4 to the vehicle device 2 or the sensor signal output from the driver biometric detection sensor 5 to the vehicle device 2 may be used to verify the physical condition abnormality determined by the dialogue agent function.

In response to the controller 25 specifying the level of physical condition abnormality, the controller 25 switches to an awakening operation execution process (S4, awakening operation execution procedure). When the controller 25 starts the awakening operation execution process, the controller 25 determines a level of the awakening operation according to the level of specified physical condition abnormality (S21), and executes the awakening operation corresponding to the determined level (S22). The controller 25 executes the awakening operation by outputting the notification command signal to the driver HMI device 3 and outputs the awakening sound from the speaker to stimulate the driver. For another example, the controller 25 may output the control signal to the air conditioning system 20 to control the air conditioning so that the air volume directed toward the driver is increased or the direction of air blow is directed toward the driver, and awakens the driver by applying the stimulus.

The controller 25 determines whether the driver's physical condition abnormality has been resolved by executing the awakening operation (S23, abnormality resolution determination procedure) In response to the controller 25 determining that the driver's physical condition abnormality has been resolved (S23: YES), the controller 25 records the driver's physical condition at that time (S24), records the content of the awakening operation executed to the driver (S25), and updates the driver data stored in the driver data storage 11. The controller 25 detects an accuracy of driving operation of the driver and concentration level of the driver (S26), and determines whether the driving operation after execution of the awakening operation is normal (S27).

In response to the controller 25 determining that the accuracy of driving operation and the concentration level of the driver is equal to or higher than a predetermined level and determining that the driving operation after execution of the awakening operation is normal (S27: YES), the controller 25 determines whether the travelling by manual driving (manual travelling) can be continued (S28). In response to the controller 25 determining that the manual travelling can be continued (S28: YES), the controller 25 confirms "manual travelling continuable" (S29) as the processing result of the awakening operation execution process, and ends the awakening operation execution process.

In response to the controller 25 determining that the driver's physical condition abnormality has not been resolved (S23: NO), the controller 25 increases the level of the awakening operation (S30), and executes the awakening operation corresponding to the increased level (S31). The controller 25 determines whether the driver's physical condition abnormality has been resolved by executing the awakening operation (S32). In response to the controller 25 determining that the driver's physical condition abnormality has been resolved (S32: YES), the controller 25 executes the above-described process in S24 and subsequent process.

In response to the controller 25 determining that the driver's physical condition abnormality has not been resolved (S32: NO), the controller 25 determines whether an upper limit of the level of the awakening operation has been reached (S33). In response to the controller 25 determining that the upper limit has not been reached (S33: NO), the controller 25 returns to S30, and repeats the process in S30 and subsequent process. In response to the controller 25 determining that the level of awakening operation has reached the upper limit (S33: YES), the controller 25 records the driver's physical condition at that time (S34), records the content of the awakening operation executed to the driver (S35), and updates the driver data stored in the driver data storage 11. The controller 25 confirms "manual travelling not continuable" (S36) as the processing result of the awakening operation execution process, and ends the awakening operation execution process.

When the controller 25 specifies that the accuracy of the driving operation of the driver and the concentration level of the driver are lower than predetermined levels and the driving operation after execution of the awakening operation is still abnormal (S27: NO), the controller 25 confirms "manual travelling not continuable" (S36) as the processing result of the awakening operation execution process, and ends the awakening operation execution process. In response to the controller 25 determining that the manual travelling cannot be continued (S28: NO), the controller 25 confirms "manual travelling not continuable" (S36) as the processing result of the awakening operation execution process, and ends the awakening operation execution process.

The controller 25 confirms the processing result of the awakening operation execution process after ending the awakening operation execution process (S5). In response to the controller 25 specifying that the processing result of the awakening operation execution process is "manual travelling continuable" and determines that the driver's physical condition abnormality has been resolved by executing the awakening operation execution process (S5: YES), the controller 25 ends the current driver monitoring process, and waits for the establishment of the start even of the next driver monitoring process.

In response to the controller 25 specifying that the processing result of the awakening operation execution process is "manual travelling not continuable" but not "manual travelling continuable", and determines that the driver's physical condition abnormality has not been resolved although the awakening operation execution process is executed (S5: NO), the controller 25 switches to an autonomous travelling start process (S6).

When the controller 25 starts the autonomous travelling start process, the controller 25 outputs the autonomous travelling mode signal to the travelling control system 21, controls the vehicle to travel in the autonomous travelling mode, starts the vehicle travelling in the autonomous travelling mode, and starts the emergency autonomous travelling (S41, emergency autonomous travelling execution procedure). Thus, the vehicle switches from the manual travelling to the autonomous travelling, and continues the travelling by starting the autonomous travelling in the autonomous travelling mode. Here, it is premised that other conditions for switching from the manual travelling to the autonomous travelling, for example, a condition that the current position of the vehicle is within an autonomous travelling area, have already been satisfied.

When the emergency autonomous travelling is started, the controller 25 searches the driver data stored in the driver data storage 11 (S42) and estimates the reason of the currently detected physical condition abnormality (S43). When the symptom which is the reason of the currently detected physical condition abnormality corresponds to a symptom related to the past medical history stored in the driver data storage 11, the controller 25 estimates that the reason of the currently detected physical condition abnormality corresponds to the past medical history. When the symptom which is the reason of the currently detected physical condition abnormality does not correspond to any one of the past medical history stored in the driver data storage 11, the controller 25 estimates that the reason of the currently detected physical condition abnormality is a new medical history. The controller 25 may implement the estimation of the reason of the currently detected physical condition abnormality by using the artificial intelligence technology After the controller 25 estimates the reason of the currently detected physical condition abnormality, the controller 25 outputs a search signal to the navigation ECU 19 to search for a facility that can treat the driver's physical condition abnormality (S44). When the controller 25 estimates that the reason of the currently detected physical condition abnormality corresponds to the past medical history, the controller 25 controls the navigation ECU 19 to search for a medical institution (for example, internal medicine, neurology, etc.) that can specially examine the corresponding symptom. When the controller 25 estimates that the reason of the currently detected physical condition abnormality is a new medical history, the controller 25 controls the navigation ECU 19 to search for a comprehensive medical institution capable of diagnosing a wide range of symptoms. In this case, the controller 25 considers the travel time, and searches for the facility within a limited area where the travel time is within a predetermined time. In addition, the controller 25 may refer to the driver's hospital visit history. When there is a medical institution that has visited by the driver in the past, the controller 25 controls the navigation ECU to search for the medical institution that has visited by the driver.

In response to a medical institution being specified as a facility capable of treating the driver's physical condition abnormality by the navigation ECU 19 (S45: YES), the controller 25 controls the navigation ECU 19 to set the specified medical institution as the destination (S46). The controller 25 controls the navigation ECU to search for a route from the current position of the vehicle to the specified medical institution (S47), perform route guidance according to the searched route (S48), and ends the autonomous travelling start process.

Figure 7:
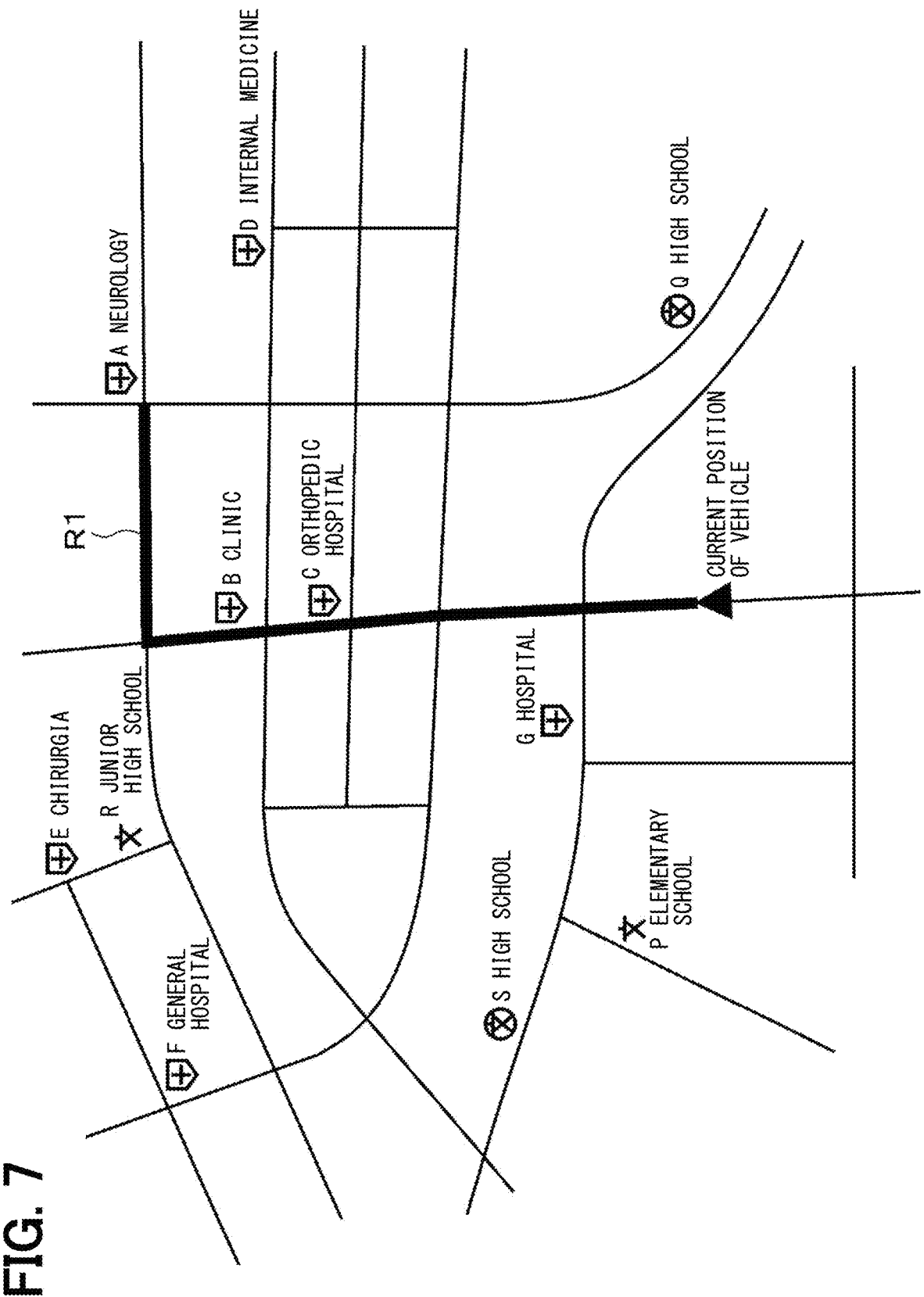
FIG. 7 is a diagram (first example) showing a route from a current position of a vehicle to a medical institution.
Figure 8:
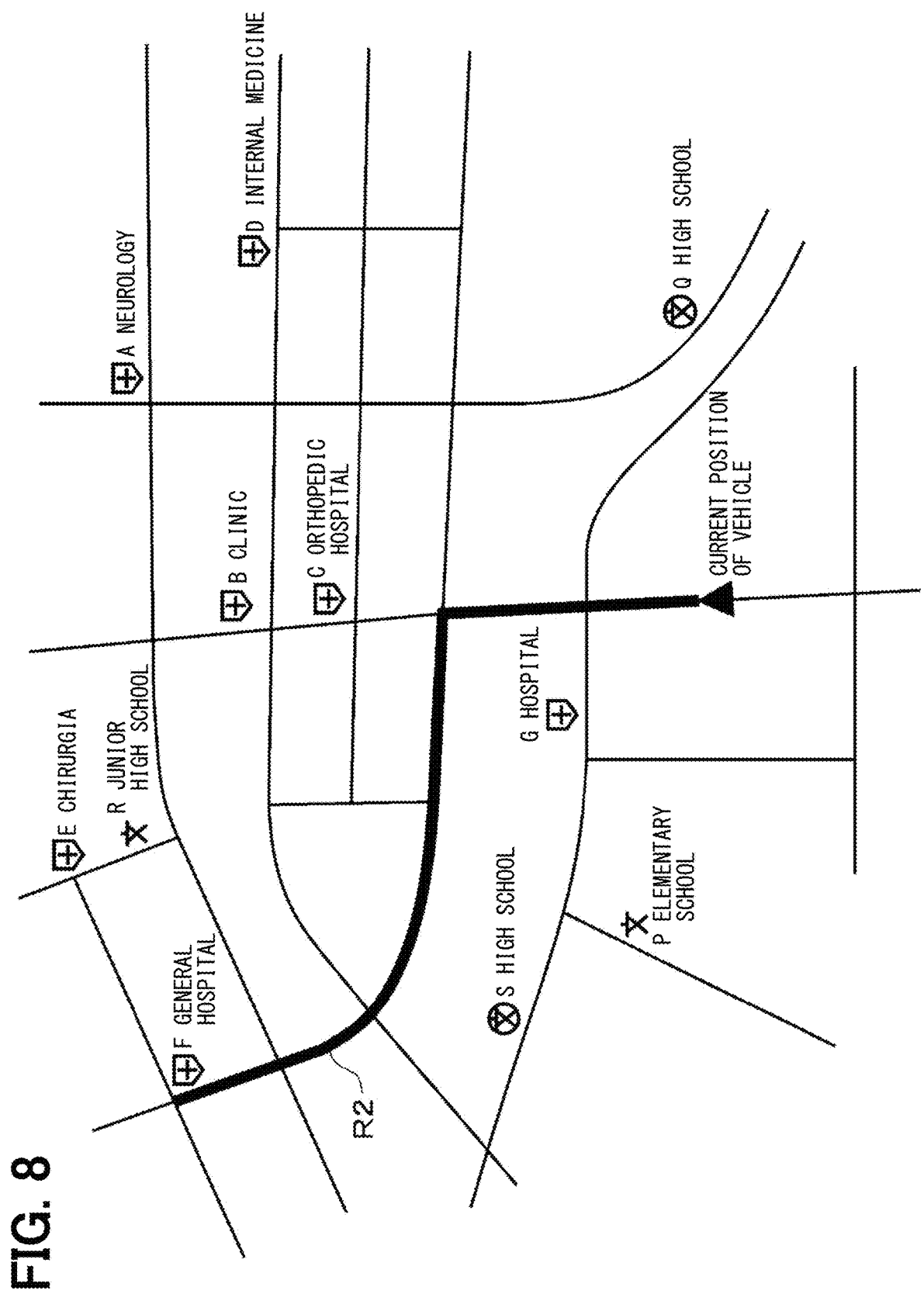
FIG. 8 is a diagram (second example) showing a route from a current position of a vehicle to a medical institution.

As shown in FIG. 7, when the navigation ECU 19 specifies, for example, "neurology clinic A" as a medical institution that can perform professional medical examination, the navigation ECU 19 searches for a route from the current position of the vehicle to the "neurology clinic A". When the vehicle succeeds in searching for the route R1 from the current position to the "neurology clinic A", the vehicle starts autonomous traveling according to the specified route R1. As shown in FIG. 8, when the navigation ECU 19 specifies, for example, a "general hospital F" as a medical institution that can perform general medical examination, the navigation ECU 19 searches for a route from the current position of the vehicle to the "general hospital F". When the vehicle succeeds in searching for the route R2 from the current position to the "general hospital F", the vehicle starts autonomous traveling according to the specified route R2. When the medical institution is set as the destination as described above, the controller 25 may send a telephone call or an e-mail to the medical institution, notify an arrival of the vehicle, and ask for preparation to accept the driver.

In response to a medical institution being not specified as a facility capable of treating the driver's physical condition abnormality by the navigation ECU 19 (S45: NO), the controller 25 controls the navigation ECU 19 to set a facility which is not a medical institution as the destination (S49). The controller 25 controls the navigation ECU to search for a route from the current position of the vehicle to the facility (S50), perform route guidance according to the searched route (S51), and ends the autonomous travelling start process.

Figure 9:
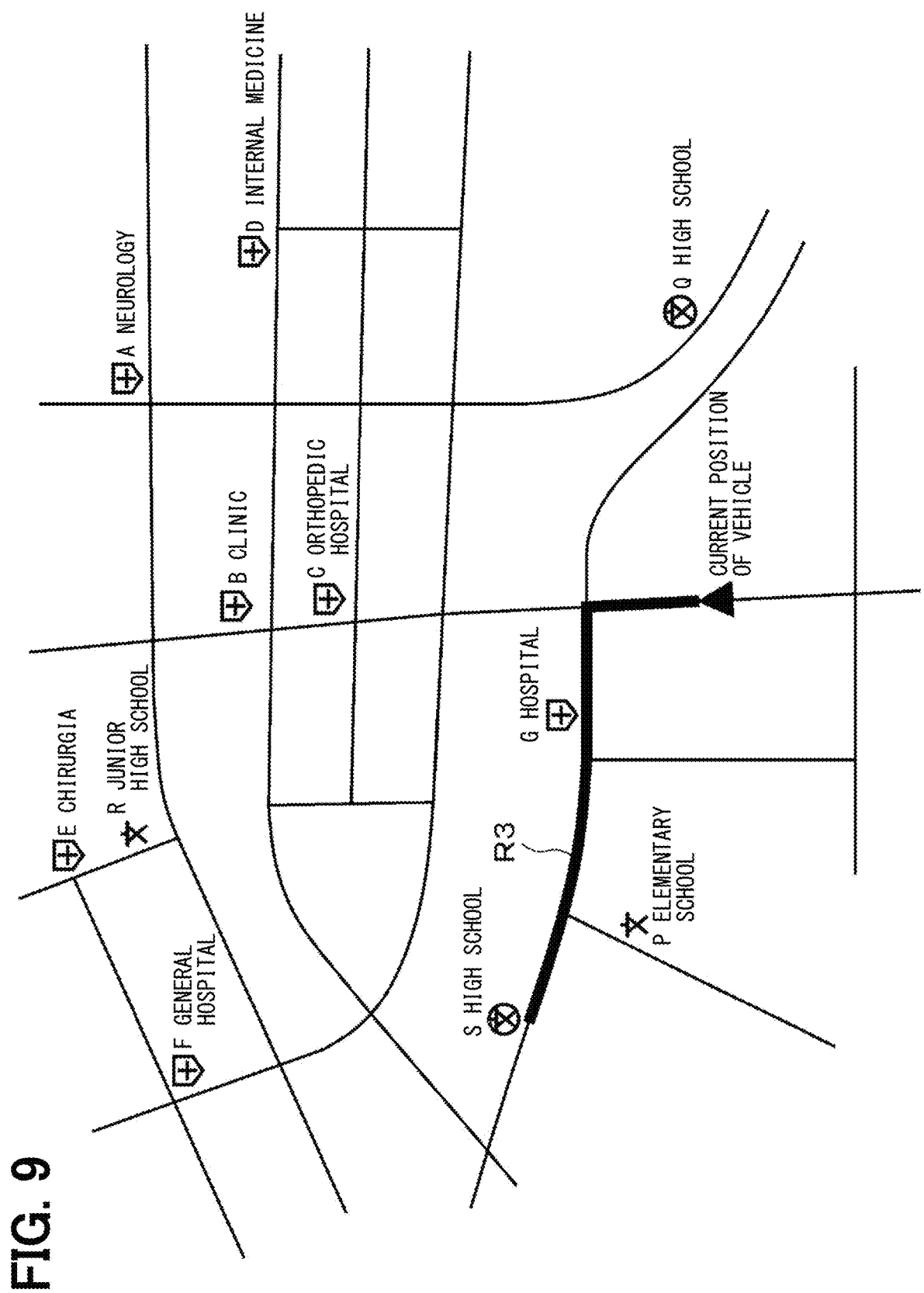
FIG. 9 is a diagram showing a route from a current position of a vehicle to another facility different from the medical institution.

As shown in FIG. 9, when the navigation ECU 19 specifies, for example, "high school S" as a facility which is not the medical institution, the navigation ECU 19 searches for a route from the current position of the vehicle to the "high school S". When the vehicle succeeds in searching for the route R3 from the current position to the "high school S", the vehicle starts autonomous traveling according to the specified route R3. When the facility which is not the medical institution is set as the destination as described above, the controller 25 may send a telephone call or an e-mail to the facility, notify an arrival of the vehicle, and ask for preparation to accept the vehicle.

In response to the controller 25 finishing the autonomous travelling start process and starting the emergency autonomous travelling to the destination, the controller 25 starts a rescue request in traveling state (S7). When the controller 25 starts the rescue request start process in the travelling state, the controller 25 outputs the dialogue command signal to the vehicle peripheral HMI device 8 and starts the rescue request in traveling state. The controller 25 projects an image on a rear window or a side window of the vehicle which functions as a window display, and displays a message indicating a rescue request in traveling state toward the outer surrounding of the vehicle (S61).

Figure 10:
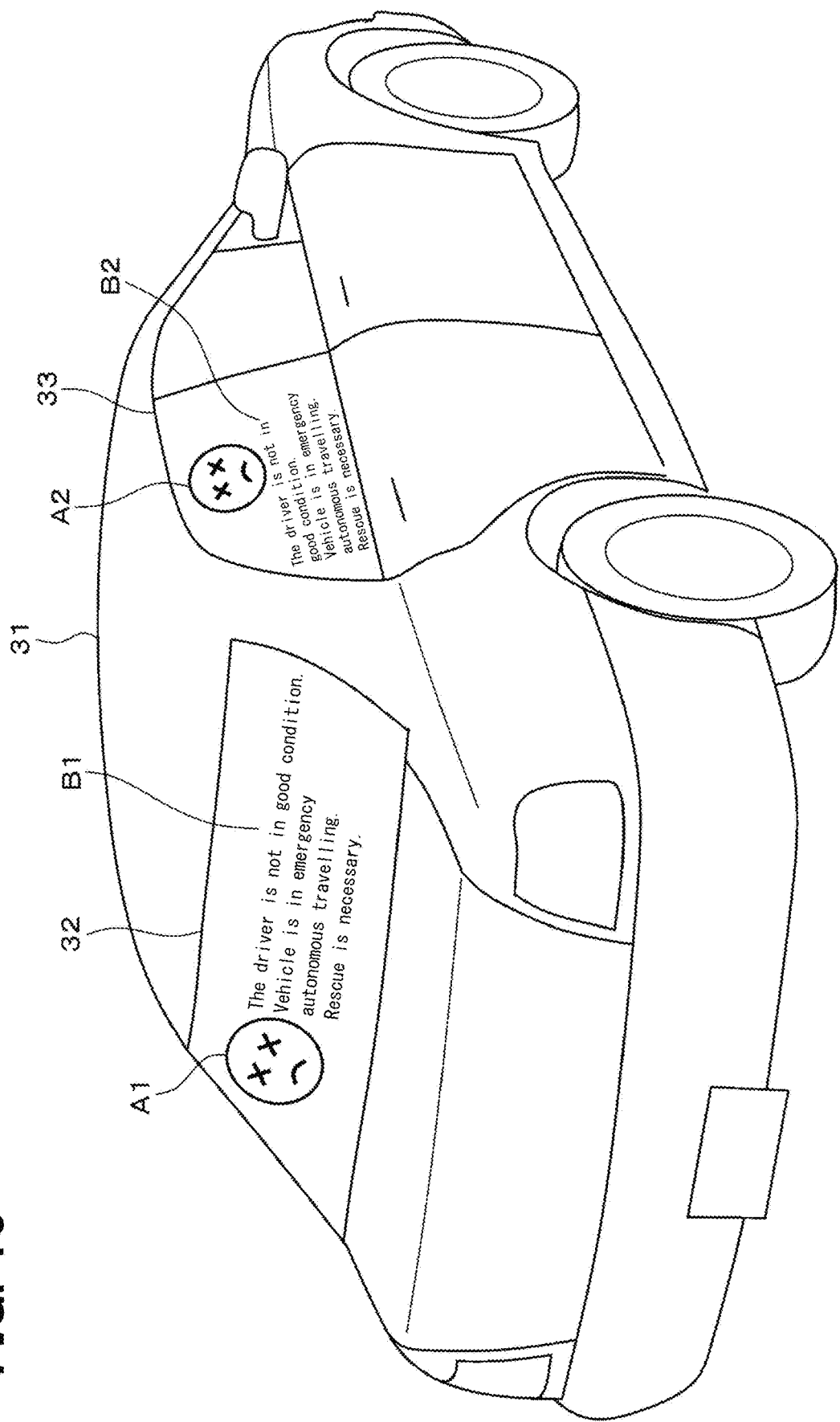
FIG. 10 is a diagram showing a notification of a rescue request in traveling state.

As shown in FIG. 10, the controller 25 displays a face image A1, A2 and a message B1, B2 indicating the physical condition abnormality of the driver on the rear window 32 or the side window 33 of the vehicle 31. For example, the message may be "The driver is not in good condition. Vehicle is in emergency autonomous travelling. Rescue is necessary". By displaying the face image A1, A2 and the message B1, B2, drivers of other vehicles and pedestrians can be notified of that the subject vehicle is in emergency autonomous travelling and the driver needs help. Thus, the emergency autonomous travelling of the subject vehicle can be prevented from being interfered by surrounding of the subject vehicle. For another example, a display device may be attached to a roof of the vehicle 31 and the face image A1, A2 and the message B1, B2 may be displayed on the display device.

The controller 25 outputs a transmission command signal to the communication device 9 which instructs the communication device 9 to transmit a message signal, which indicates a rescue request in travelling state, to the server 12, the communication device 13 of different vehicle, and the portable terminal 14 of the pedestrian (S62). Then, rescue request start process in the traveling state is ended.

Figure 11:
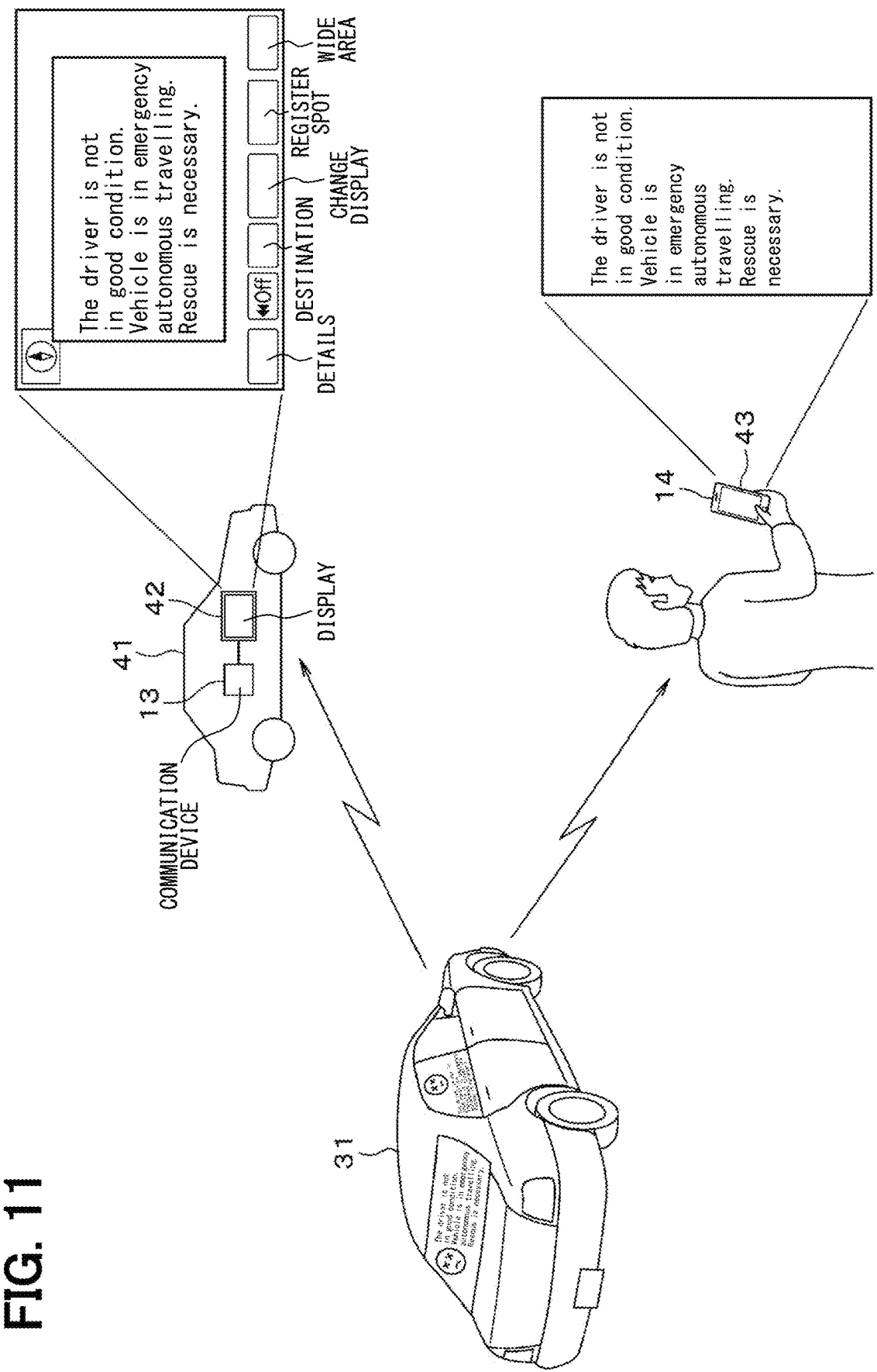
FIG. 11 is a diagram showing a transmission of message signal indicating a rescue request during traveling.

As shown in FIG. 11, when the message signal transmitted from the communication device 9 of the subject vehicle is received by the communication device 13 of different vehicle 41, a display device 42 of different vehicle 41 may display the content of the received message signal. When the message signal transmitted from the communication device 9 of the subject vehicle is received by the pedestrian's portable terminal 14, a display screen 43 of the portable terminal 14 may display the content of the received message signal. By displaying the message of rescue request in travelling state of the subject vehicle on the display device 42 of different vehicle 41 or on the display screen 43 of the portable terminal 14, a driver of different vehicle or the pedestrian can be notified of that the subject vehicle is in emergency autonomous travelling and the driver needs help. Thus, the emergency autonomous travelling of the subject vehicle can be prevented from being interfered by surrounding of the subject vehicle.

In order to reduce power consumption of a vehicle battery, the controller 25 may display the message of rescue request in traveling state toward the outside surrounding of the vehicle only when presence of another vehicle or pedestrian is detected around the subject vehicle. In order to reduce power consumption of the vehicle battery, the controller 25 may transmit the message signal indicating rescue request in traveling state from the communication device 9 of the subject vehicle to the communication device 13 of another vehicle or to the portable terminal 14 of pedestrian only when presence of another vehicle or pedestrian is detected around the subject vehicle.

After the controller 25 ends the rescue request start processing in the traveling state, the controller 25 returns to S8 and determines whether the vehicle has arrived at the destination (S8). When the controller 25 determines that the vehicle has arrived at the destination (S8: YES), the controller 25 ends the emergency autonomous travelling (S9) and the rescue request in traveling state (S10). Then, the controller 25 determines whether to start and execute a rescue request after arrival (S11).

In a case where a medical institution is set as the destination and after the vehicle arrives at the medical institution, the controller 25 determines that the medical institution is capable of promptly taking measures against the driver's physical condition abnormality by the staff of the medical institution. Thus, the controller 25 determines that it is not necessary to execute the rescue request start process after arrival (S11: NO). Then, the controller ends the driver monitoring process.

In a case where a facility different from a medical institution is set as the destination and after the vehicle arrives at the facility, the controller 25 determines that the facility is less likely to promptly take measures against the driver's physical condition abnormality. Thus, the controller 25 determines that it is necessary to execute the rescue request start process after arrival (S11: YES). Then, the controller 25 executes the rescue request after arrival (S12)

When the controller 25 starts the rescue request start process after arrival, the controller 25 outputs the dialogue command signal to the vehicle peripheral HMI device 8 and starts the rescue request after arrival. The controller 25 projects an image on the rear window or the side window of the vehicle which functions as the window display, and displays a message indicating a rescue request after arrival toward the outer surrounding of the vehicle (S71).

Figure 12:
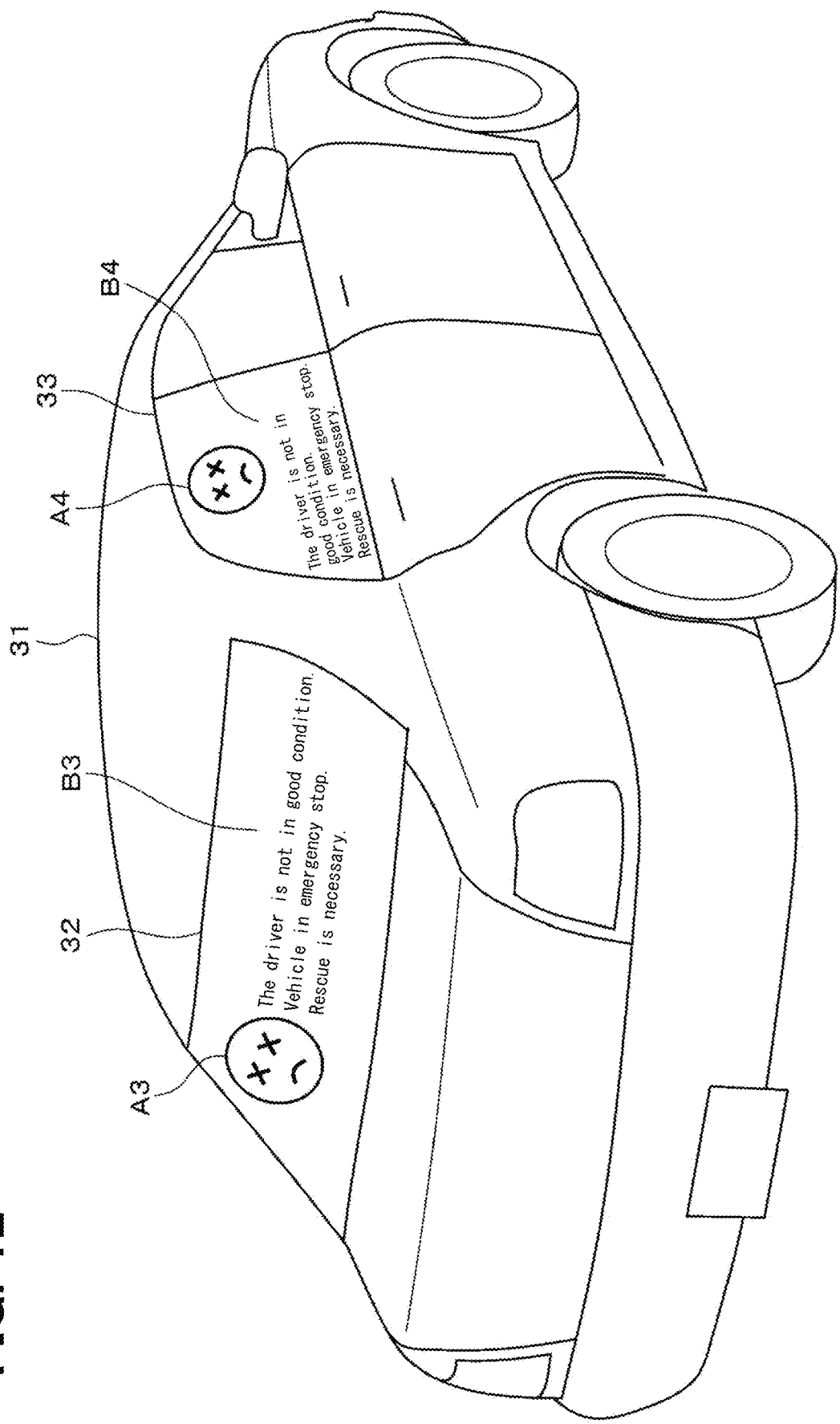
FIG. 12 is a diagram showing a notification of a rescue request after arrival.

As shown in FIG. 12, the controller 25 displays a face image A3, A4 and a message B3, B4 indicating the physical condition abnormality of the driver on the rear window 32 or the side window 33 of the vehicle 31. For example, the message may be "The driver is not in good condition. Vehicle in emergency stop. Rescue is necessary." By displaying the face image A3, A4 and the message B3, B4, drivers of other vehicles and pedestrians can be notified of that the subject vehicle is in emergency stop and the driver needs help.

The controller 25 outputs a transmission command signal to the communication device 9 which instructs the communication device 9 to transmit a message signal, which indicates a rescue request after arrival, to the server 12, the communication device 13 of different vehicle, and the portable terminal 14 of the pedestrian (S72). Then, the rescue request start process after arrival is ended.

Figure 13:
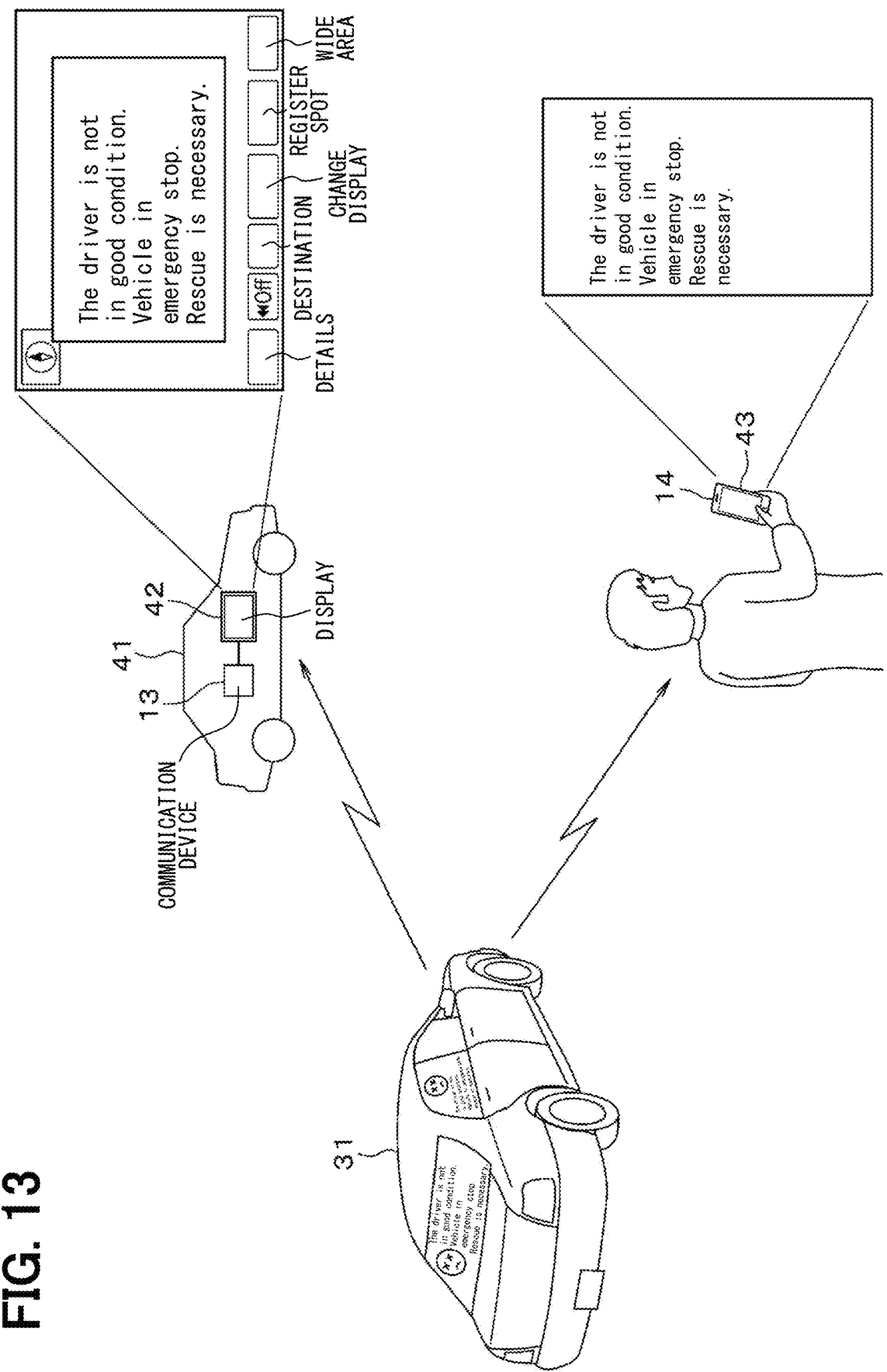
FIG. 13 is a diagram showing a transmission of message signal indicating a rescue request after arrival.

As shown in FIG. 13, when the message signal transmitted from the communication device 9 of the subject vehicle is received by the communication device 13 of different vehicle 41, the display device 42 of different vehicle 41 may display the content of the received message signal. When the message signal transmitted from the communication device 9 of the subject vehicle is received by the pedestrian's portable terminal 14, the display screen 43 of the portable terminal 14 may display the content of the received message signal. By displaying the message of rescue request after arrival of the subject vehicle on the display device 42 of different vehicle 41 or on the display screen 43 of portable terminal 14, a driver of different vehicle or the pedestrian can be notified of that the subject vehicle is in emergency stop and the driver needs help.

In order to reduce power consumption of the vehicle battery, the controller 25 may display the message of rescue request after arrival toward the outside surrounding of the vehicle only when presence of another vehicle or pedestrian is detected around the subject vehicle. In order to reduce power consumption of the vehicle battery, the controller 25 may transmit the message signal indicating rescue request after arrival from the communication device 9 of the subject vehicle to the communication device 13 of another vehicle or to the portable terminal 14 of pedestrian only when presence of another vehicle or pedestrian is detected around the subject vehicle.

The embodiment described above can provide effects as below.

In the vehicle device 2, when the driver's physical condition becomes abnormal in the travelling state, an awakening operation is executed. When the driver's abnormal physical condition is not resolved even after the awakening operation is executed, instead of applying a brake control to stop the vehicle, the vehicle is controlled to travel in the autonomous travelling mode for executing the emergency autonomous travelling. By activating the autonomous travelling of the vehicle, it is possible to avoid a situation which may cause confusion or an accident around the vehicle. As a result, when the driver's physical condition is specified to be abnormal in a travelling state of the vehicle, appropriate measures can be taken with consideration of the influence of the vehicle to the surrounding of the vehicle.

In the vehicle device 2, during the execution of emergency autonomous travelling, the execution of emergency autonomous travelling is notified toward the surrounding of the vehicle, and the rescue request in travelling state is executed toward the surrounding of the vehicle. With this configuration, it is possible to notify the drivers of other vehicles and pedestrians that the subject vehicle is in the emergency autonomous travelling and the driver of the subject vehicle needs help.

When determining that the driver's physical condition abnormality has not been resolved, the vehicle device 2 searches for a facility that can treat the driver's physical condition abnormality. When a medical institution is specified as the facility that can treat the driver's physical condition abnormality, the specified medical institution is set as the destination, and emergency autonomous travelling is carried out toward the set destination. In this configuration, a medical institution is set as the destination and emergency autonomous travelling to the medical institution is carried out. Thus, it is possible to promptly take measures against the driver's physical condition abnormality after arriving at the set medical institution.

In a case were the vehicle device 2 fails to find a medical institution that is capable of treating the driver's physical condition abnormality, the vehicle device 2 sets a facility which is not a medical institution as the destination and executes the emergency autonomous travelling. With this configuration, in a case where a medical institution cannot be as the destination, a facility which is not the medical institution can be set as the destination and the emergency autonomous travelling is carried out to the set facility as the destination. Thus, the subject vehicle can wait for an arrival of an ambulance or an emergency helicopter at the facility and the prompt measures against the driver's physical condition abnormality.

After the vehicle arrives at the facility which is not the medical institution, the vehicle device 2 executes a rescue request after arrival toward the surrounding of the vehicle. With this configuration, it is possible to notify the drivers of other vehicles and pedestrians that the subject vehicle is in the emergency stop and the driver of the subject vehicle needs help.

While the present disclosure has been described based on the embodiment, the present disclosure is not limited to the embodiment or structure described herein. The present disclosure incorporates various modifications and variations within the scope of equivalents. Additionally, various combinations and configurations, as well as other combinations and configurations including more, less, or only a single element, are within the scope and spirit of the present disclosure.

When the emergency autonomous travelling is started, the vehicle device may be configured to send a telephone call or an e-mail to a destination such as a family member or an acquaintance registered in advance.

In a case where the facility to be searched is limited within a predetermined area where the travel time is within the predetermined time, the travel time may be adjustably determined according to the level of driver's physical condition abnormality. When the risk level of driver's physical condition abnormality is relatively low, the travel time may be set to a relatively long time. When the risk level of the driver's physical condition abnormality is relatively high, the travel time may be set to a relatively short time.

The vehicle device may determine whether a parking place is available within the medical institution. When determining that a parking place is available within the medical institution, the medical institution is set as the destination. When determining that a parking space is unavailable, the destination is set as a place around the medical institution where the vehicle can be parked.

In another example, an in-vehicle camera may capture an image of the vehicle compartment, and the vehicle device may determine from the image taken by the in-vehicle camera presence of another occupant in the vehicle compartment. When determining absence of another occupant, the destination may be automatically set. When determining presence of another occupant, multiple candidates may be displayed to the occupant, and the occupant may select one candidate as the destination from the multiple candidates.

In the foregoing embodiment, an image is projected onto the rear window or on the side window of the vehicle to form the window display. Alternatively, a movable display may be installed to the vehicle. The movable display moves to a predetermined position where the display is viewable from outside of the vehicle only when the rescue request is activated. By this configuration, the message indicating the rescue request in travelling state or the message indicating the rescue request after arrival can be displayed toward the outside surrounding of the vehicle and viewable from surrounding of the vehicle.

As another example, a character used in the dialogue agent function may be provided with an emotional expression function to express various emotions. For example, the facial expression of the character may be changed according to the level of the driver's physical condition to notify the level of emergency and deterioration or recovery of the driver's physical condition. The face image or the message indicating that the driver is in abnormal physical condition may be any face image or message as long as it can expresses that the driver is in abnormal physical condition. For example, the message may be "Emergency, please call an ambulance immediately." In addition, the emergency may be notified by color classification. When the emergency is relatively high urgent level, the face image or the message may be notified in red. When the emergency is relatively low urgent level, the face image or the message may be notified in yellow. Further, in addition to the face image and the message, specific numerical values indicating the driver's pulse, heart rate, blood pressure or the like may be notified toward surrounding of the vehicle.

The controller and method described in the present disclosure may be implemented by a special purpose computer which includes a memory and a processor programmed to execute one or more functions embodied in computer programs of the memory. Alternatively, the controller and method described in the present disclosure may be implemented by a special purpose computer which includes a processor with one or more dedicated hardware logic circuits. Alternatively, the controller and method described in the present disclosure may be implemented by one or more special purpose computers, which is configured as a combination of a processor and a memory, which are programmed to perform one or more functions, and a processor which is configured with one or more hardware logic circuits. The computer program may also be stored in a computer readable non-transitory tangible storage medium as instructions to be executed by a computer.

What is claimed is:

1. A vehicle device comprising:
a physical condition monitoring unit configured to monitor a physical condition of a driver in a driving state of a vehicle;
an awakening operation execution unit configured to execute an awakening operation in response to the physical condition of the driver being determined to be abnormal by the physical condition monitoring unit;
an abnormality resolution determination unit configured to determine whether the abnormal physical condition of the driver is resolved by the awakening operation executed by the awakening operation execution unit;
a travelling control unit configured to control the vehicle to travel in a manual travelling mode or in an autonomous travelling mode;
an emergency autonomous travelling execution unit configured to execute an emergency autonomous travelling of the vehicle by instructing the travelling control unit to control the vehicle travel in the autonomous travelling mode in response to the abnormality resolution determination unit determining that the abnormal physical condition of the driver is not resolved;
an emergency autonomous travelling notification unit configured to notify a surrounding of the vehicle that the vehicle is in a state of the emergency autonomous travelling while the emergency autonomous travelling execution unit executes the emergency autonomous travelling of the vehicle;
a first rescue request execution unit configured to execute a first rescue request which indicates the driver is having an ongoing emergency situation in travelling state toward the surrounding of the vehicle while the emergency autonomous travelling execution unit executes the emergency autonomous travelling of the vehicle;
a facility search unit configured to search for a facility capable of treating the abnormal physical condition of the driver in response to the abnormality resolution determination unit determining that the abnormal physical condition of the driver is not resolved; and
a second rescue request execution unit configured to execute a second rescue request which indicates the driver is having an ongoing emergency situation after arrival toward the surrounding of the vehicle in response to the vehicle arriving at another facility and being stopped, the second rescue request after arrival being different from the first rescue request in travelling state, wherein
the emergency autonomous travelling execution unit sets the facility specified by the facility search unit as a destination in response to the facility search unit specifying the facility capable of treating the abnormal physical condition of the driver, and executes the emergency autonomous travelling of the vehicle to the destination,
the emergency autonomous travelling execution unit sets the another facility as a destination in response to the facility search unit failing to specify the facility capable of treating the abnormal physical condition of the driver, and executes the emergency autonomous travelling of the vehicle to the destination,
the emergency autonomous travelling notification unit displays, toward an outer surrounding of the vehicle, a message, including a description of the emergency in the form of a text and/or an image, indicating that the vehicle is in an emergency autonomous travelling state and the driver needs rescue,
in response to determining that the vehicle has arrived at the destination, the emergency autonomous travelling execution unit ends the emergency autonomous travelling and the first rescue request execution unit ends the first rescue request in travelling state, and then the second rescue request execution unit determines whether to start and execute the second rescue request after arrival, and
in response to determining that the second rescue request after arrival is necessary to be started and executed, the second rescue request execution unit starts and executes the second rescue request after arrival.

2. The vehicle device according to claim 1, wherein
the first rescue request execution unit executes the first rescue request in travelling state toward the surrounding of the vehicle by a dialogue agent function which projects a combination of either or both text and images which provide information as to the driver's state.

3. The vehicle device according to claim 1, wherein
the second rescue request execution unit executes the second rescue request after arrival toward the surrounding of the vehicle by a dialogue agent function which projects a combination of either or both text and images which provide information as to the driver's state.

4. The vehicle device according to claim 1, wherein the message indicating that the vehicle is in the emergency autonomous travelling state and the driver needs rescue is projected on a rear window or a side window of the vehicle toward the outer surrounding of the vehicle and/or is displayed toward the outer surrounding of the vehicle on a display device, which is attached to an outer portion of the vehicle.

5. The vehicle device according to claim 1, wherein
when the another facility, which is not a medical institution capable of treating the abnormal physical condition of the driver, is set as the destination and the vehicle arrives and stops at the destination by the emergency autonomous travelling, the second rescue request execution unit determines that the second rescue request after arrival is necessary to be started and executed.

6. The vehicle device according to claim 1, wherein
the emergency autonomous travelling notification unit displays the message toward the outer surrounding of the vehicle only when presence of another vehicle or pedestrian is detected around the vehicle, wherein the detection is based on a predetermined range of a vehicle peripheral detection sensor.

7. A drive assist program product, which is stored in a tangible non-transitory computer-readable storage medium and comprising instructions to be executed by a controller of a vehicle device, the instructions comprising:
monitoring a physical condition of a driver in a driving state of a vehicle;

executing an awakening operation in response to the physical condition of the driver being determined to be abnormal;

determining whether the abnormal physical condition of the driver being resolved by an execution of the awakening operation;

executing an emergency autonomous travelling of the vehicle by controlling the vehicle to travel in an autonomous travelling mode in response to the abnormal physical condition of the driver being determined to be not resolved by the execution of the awakening operation;

notifying a surrounding of the vehicle that the vehicle is in a state of the emergency autonomous travelling while the emergency autonomous travelling is being executed;

executing a first rescue request which indicates the driver is having an ongoing emergency situation in travelling state toward the surrounding of the vehicle while the emergency autonomous travelling is being executed;

searching for a facility capable of treating the abnormal physical condition of the driver in response to the abnormal physical condition of the driver being determined to be not resolved;

setting the facility capable of treating the abnormal physical condition of the driver as a destination in response to the facility capable of treating the abnormal physical condition of the driver being specified and executing the emergency autonomous travelling of the vehicle to the destination;

setting another facility as a destination in response to no facility capable of treating the abnormal physical condition of the driver being specified and executing the emergency autonomous travelling of the vehicle to the destination;

executing a second rescue request which indicates the driver is having an ongoing emergency situation after arrival toward the surrounding of the vehicle in response to the vehicle arriving at the another facility and being stopped, the second rescue request after arrival being different from the first rescue request in travelling state; and displaying, toward an outer surrounding of the vehicle, a message, including a description of the emergency in the form of a text and/or an image, indicating that the vehicle is in an emergency autonomous travelling state and the driver needs rescue, wherein in response to determining that the vehicle has arrived at the destination, the controller ends the emergency autonomous travelling and the first rescue request in travelling state, and then determines whether to start and execute the second rescue request after arrival, and in response to determining that the second rescue request after arrival is necessary to be started and executed, the controller starts and executes the second rescue request after arrival.

8. A vehicle device comprising:

a processor that executes a computer program stored in a tangible non-transitory computer-readable storage medium, the processor being configured to:

monitor a physical condition of a driver in a driving state of a vehicle and determine whether the physical condition of the driver is abnormal;

execute an awakening operation in response to the physical condition of the driver being determined to be abnormal;

determine whether the abnormal physical condition of the driver is resolved by an execution of the awakening operation;

control the vehicle to travel in a manual travelling mode or in an autonomous travelling mode;

execute an emergency autonomous travelling of the vehicle by controlling the vehicle to travel in the autonomous travelling mode in response to the abnormal physical condition of the driver being determined to be not resolved;

notify a surrounding of the vehicle that the vehicle is in a state of the emergency autonomous travelling while the emergency autonomous travelling is being executed;

execute a first rescue request which indicates the driver is having an ongoing emergency situation in travelling state toward the surrounding of the vehicle while the emergency autonomous travelling is being executed;

search for a facility capable of treating the abnormal physical condition of the driver in response to the abnormal physical condition of the driver being determined to be not resolved;

set the facility capable of treating the abnormal physical condition of the driver as a destination in response to the facility capable of treating the abnormal physical condition of the driver being specified and executing the emergency autonomous travelling of the vehicle to the destination;

set another facility as a destination in response to no facility capable of treating the abnormal physical condition of the driver being specified and executing the emergency autonomous travelling of the vehicle to the destination;

execute a second rescue request which indicates the driver is having an ongoing emergency situation after arrival toward the surrounding of the vehicle in response to the vehicle arriving at the another facility and being stopped, the second rescue request after arrival being different from the first rescue request in travelling state; and display, toward an outer surrounding of the vehicle, a message, including a description of the emergency in the form of a text and/or an image, indicating that the vehicle is in an emergency autonomous travelling state and the driver needs rescue, wherein in response to determining that the vehicle has arrived at the destination, the processor ends the emergency autonomous travelling and the first rescue request in travelling state, and then determines whether to start and execute the second rescue request after arrival, and in response to determining that the second rescue request after arrival is necessary to be started and executed, the processor starts and executes the second rescue request after arrival.

\* \* \* \* \*